United States Patent
Munoz

(10) Patent No.: US 11,224,436 B2
(45) Date of Patent: Jan. 18, 2022

(54) HEMORRHAGE CONTROL DEVICE

(71) Applicant: Cesar Munoz, Cibolo, TX (US)

(72) Inventor: Cesar Munoz, Cibolo, TX (US)

( * ) Notice: Subject to any disclaimer, the term of this patent is extended or adjusted under 35 U.S.C. 154(b) by 0 days.

(21) Appl. No.: 16/880,581

(22) Filed: May 21, 2020

(65) Prior Publication Data

US 2021/0361291 A1    Nov. 25, 2021

(51) Int. Cl.
*A61B 17/12*    (2006.01)

(52) U.S. Cl.
CPC .. *A61B 17/12136* (2013.01); *A61B 17/12031* (2013.01); *A61B 2017/12004* (2013.01)

(58) Field of Classification Search
CPC ........ A61B 17/12136; A61B 17/12031; A61B 2017/12004; A61B 17/12099; A61B 17/42
See application file for complete search history.

(56) References Cited

U.S. PATENT DOCUMENTS

| | | |
|---|---|---|
| 6,796,993 B2 | 9/2004 | Lambroza |
| D679,804 S | 4/2013 | White |
| 9,492,150 B2 | 11/2016 | Ginn |
| 9,888,927 B2 | 2/2018 | Belfort |
| 2008/0058691 A1 | 3/2008 | Sorensen |
| 2014/0012363 A1* | 1/2014 | Franano ........... A61B 17/12109 623/1.12 |
| 2014/0142504 A1 | 5/2014 | Ramsey, III |
| 2017/0245864 A1* | 8/2017 | Franano ........... A61B 17/12136 |
| 2018/0310947 A1* | 11/2018 | Augustin ............... A61B 17/24 |
| 2019/0105057 A1* | 4/2019 | Radl ................. A61B 17/12109 |
| 2019/0261965 A1 | 8/2019 | Kabadayi |

FOREIGN PATENT DOCUMENTS

WO    WO2018086743    5/2018

* cited by examiner

*Primary Examiner* — George J Ulsh

(57) ABSTRACT

A hemorrhage control device for sealing a penetrating wound includes a tube having a connector engaged to a first end thereof. The connector can selectively engage a container so that the container is in fluidic communication with the tube. The container can selectively pressurize a fluid positioned therein so that the fluid is selectively dispensable through the tube. A shell is engaged to a second end of, and in fluidic communication with, the tube. The shell is selectively expandable from a compacted configuration wherein the shell is substantially circumferentially equivalent to the tube. The shell can be at least partially inserted into a penetrating wound in a mammal, such as a bullet wound. The shell then can be selectively expanded, as the fluid is dispensed from the container through the tube, so that the shell contacts a surface of the penetrating wound to control hemorrhaging.

11 Claims, 5 Drawing Sheets

HEMORRHAGE CONTROL DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to hemorrhage control devices and more particularly pertains to a new hemorrhage control device for sealing a penetrating wound.

(2) Description of Related Art Including Information Disclosed Under 37 CFR 1.97 and 1.98

The prior art relates to hemorrhage control devices. Prior art hemorrhage control devices may comprise inflatable tourniquets, absorbent plugs, and balloon tamponades.

BRIEF SUMMARY OF THE INVENTION

An embodiment of the disclosure meets the needs presented above by generally comprising a tube. A connector is engaged to a first end of the tube and is configured to selectively engage a container so that the container is in fluidic communication with the tube. The container is configured to selectively pressurize a fluid positioned therein so that the fluid is selectively dispensable from the container through the tube.

A shell is engaged to a second end of the tube so that the shell is in fluidic communication with the tube. The shell is selectively expandable from a compacted configuration wherein the shell is substantially circumferentially equivalent to the tube. The shell is configured to be at least partially inserted into a penetrating wound in a mammal, such as a bullet wound. The shell is configured to be selectively expanded, as the fluid is dispensed from the container through the tube, so that the shell contacts a surface of the penetrating wound to control hemorrhaging.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
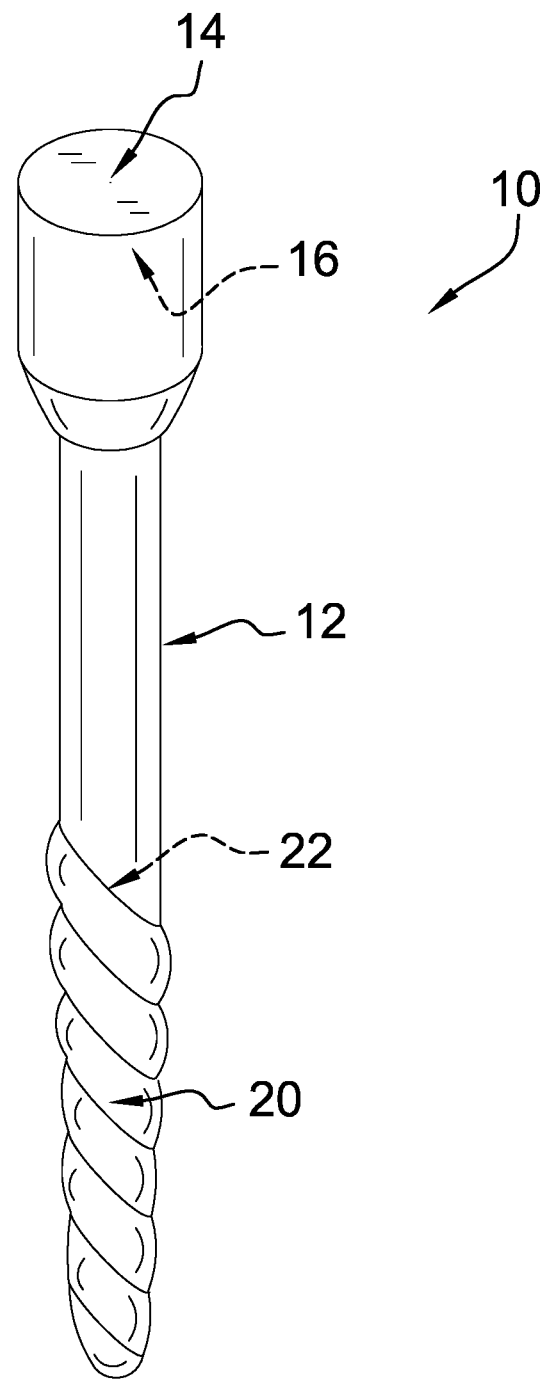
FIG. 1 is an isometric perspective view of a hemorrhage control device according to an embodiment of the disclosure.

With reference now to the drawings, and in particular to FIGS. 1 through 6 thereof, a new hemorrhage control device embodying the principles and concepts of an embodiment of the disclosure and generally designated by the reference numeral 10 will be described.

As best illustrated in FIGS. 1 through 6, the hemorrhage control device 10 generally comprises a tube 12. The tube 12 may be semirigid so that the tube 12 is resiliently bendable. The tube 12 may comprise plastic. The present invention also anticipates the tube 12 comprising rigid material, such as, but not limited to, metal, glass, and the like.

A connector 14 is engaged to a first end 16 of the tube 12 and is configured to selectively engage a container 18 so that the container 18 is in fluidic communication with the tube 12. The container 18 is configured to selectively pressurize a fluid positioned therein so that the fluid is selectively dispensable from the container 18 through the tube 12.

Figures 2, 3:
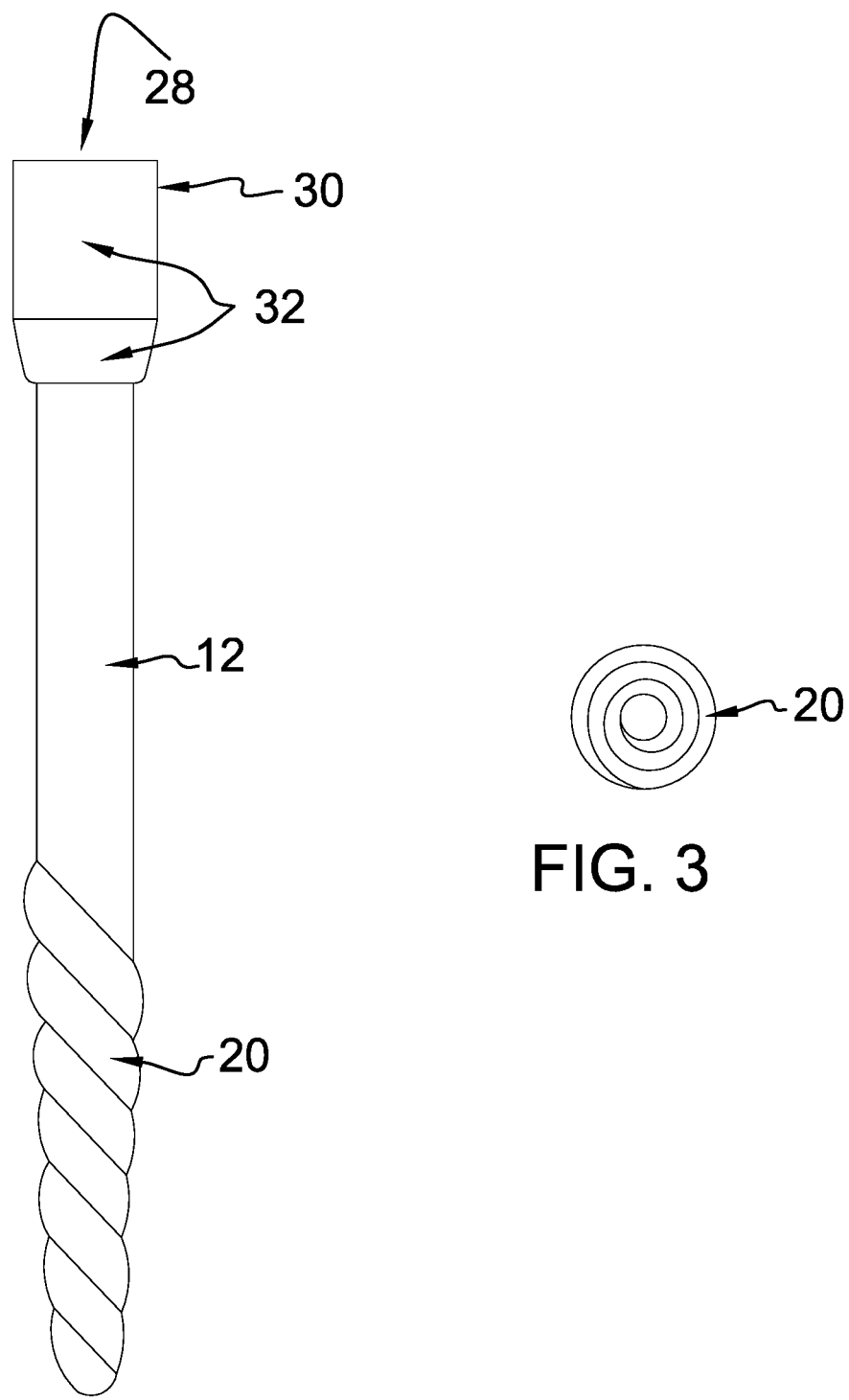
FIG. 2 is a front view of an embodiment of the disclosure.
FIG. 3 is an end view of an embodiment of the disclosure.

A shell 20 is engaged to a second end 22 of the tube 12 so that the shell 20 is in fluidic communication with the tube 12. The shell 20 is selectively expandable from a compacted configuration, as shown in FIG. 2, wherein the shell 20 is substantially circumferentially equivalent to the tube 12. The shell 20 is configured to be at least partially inserted into a penetrating wound in a mammal, such as a bullet wound. The shell 20 is configured to be selectively expanded, as the fluid is dispensed from the container 18 through the tube 12, so that the shell 20 contacts a surface of the penetrating wound to control hemorrhaging.

The present invention anticipates the fluid comprising air, or other fluidic substance, such as, but not limited to, saline, Lactated Ringers' Solution, and the like.

The shell 20 comprises at least one of polyester, nylon, polyether block amide, polyurethane, and silicone. The shell 20 may be substantially spherically shaped when filled with the fluid. The present invention also anticipates the shell 20 being alternatively shaped, such as, but not limited to, cylindrically shaped, ovoid shaped, and the like. The shell 20 may be radiopaque so that the shell 20 does not interfere with imaging procedures.

Figure 4:
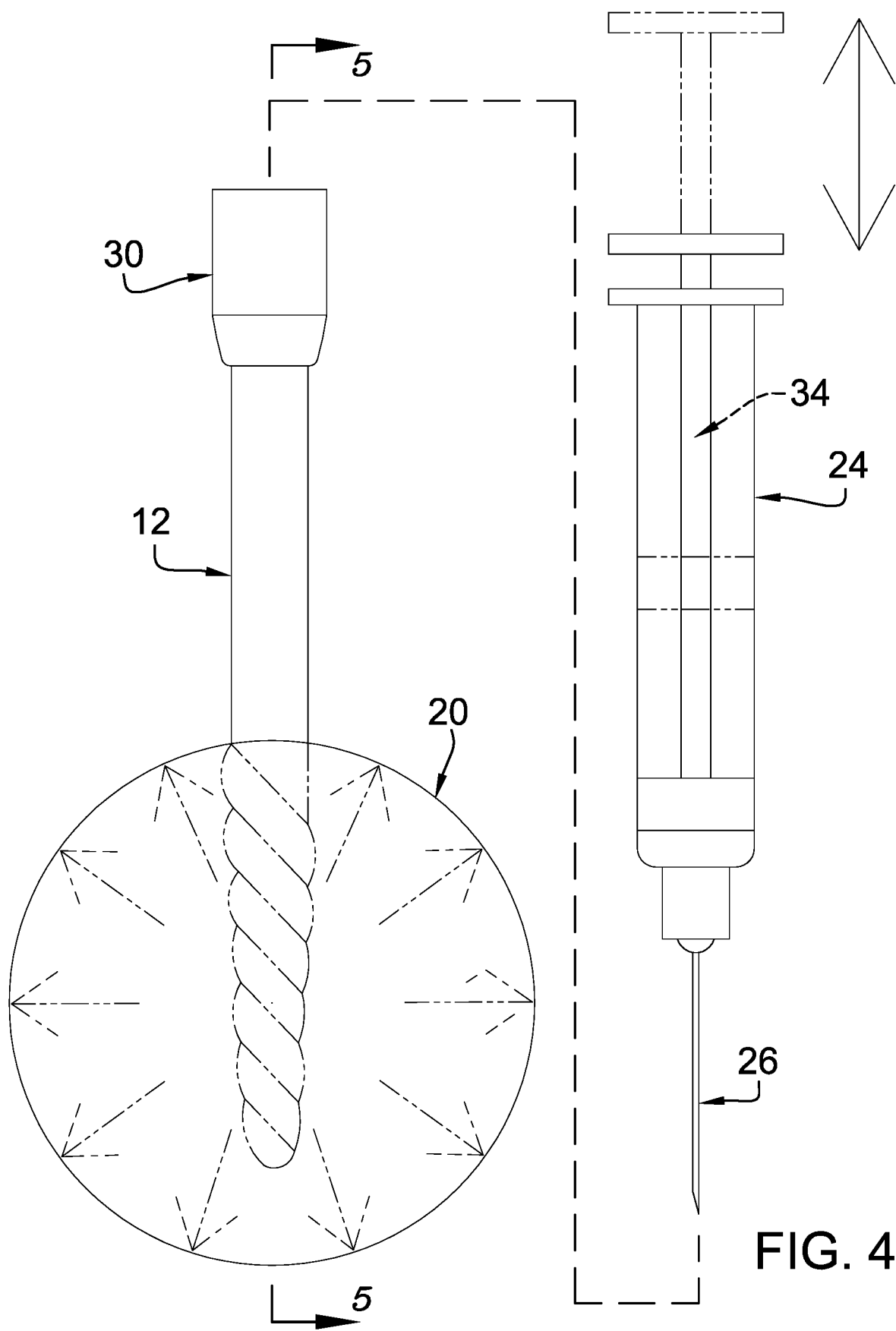
FIG. 4 is a detail view of an embodiment of the disclosure.
Figure 5:
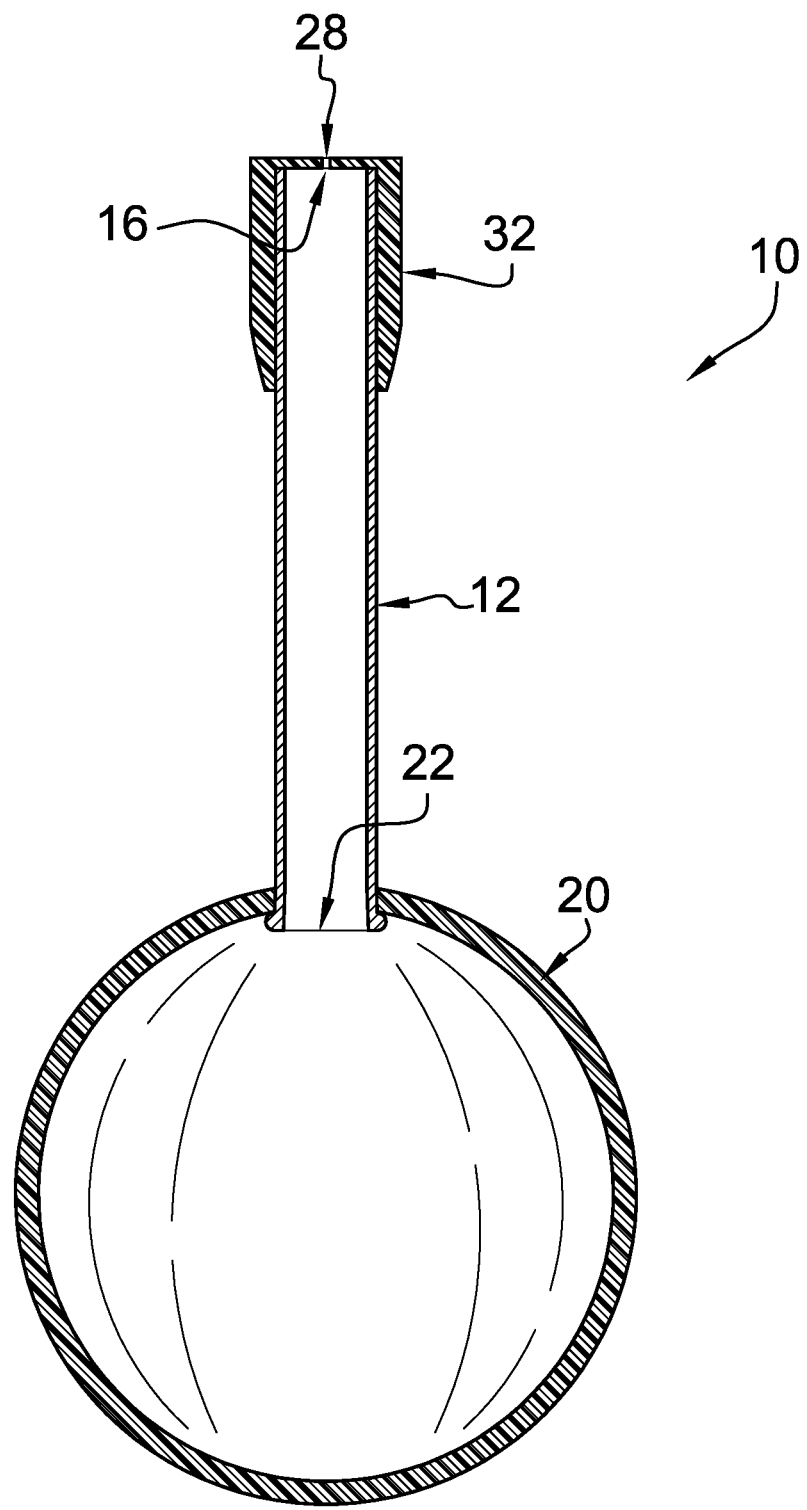
FIG. 5 is a cross-sectional view of an embodiment of the disclosure.
Figure 6:
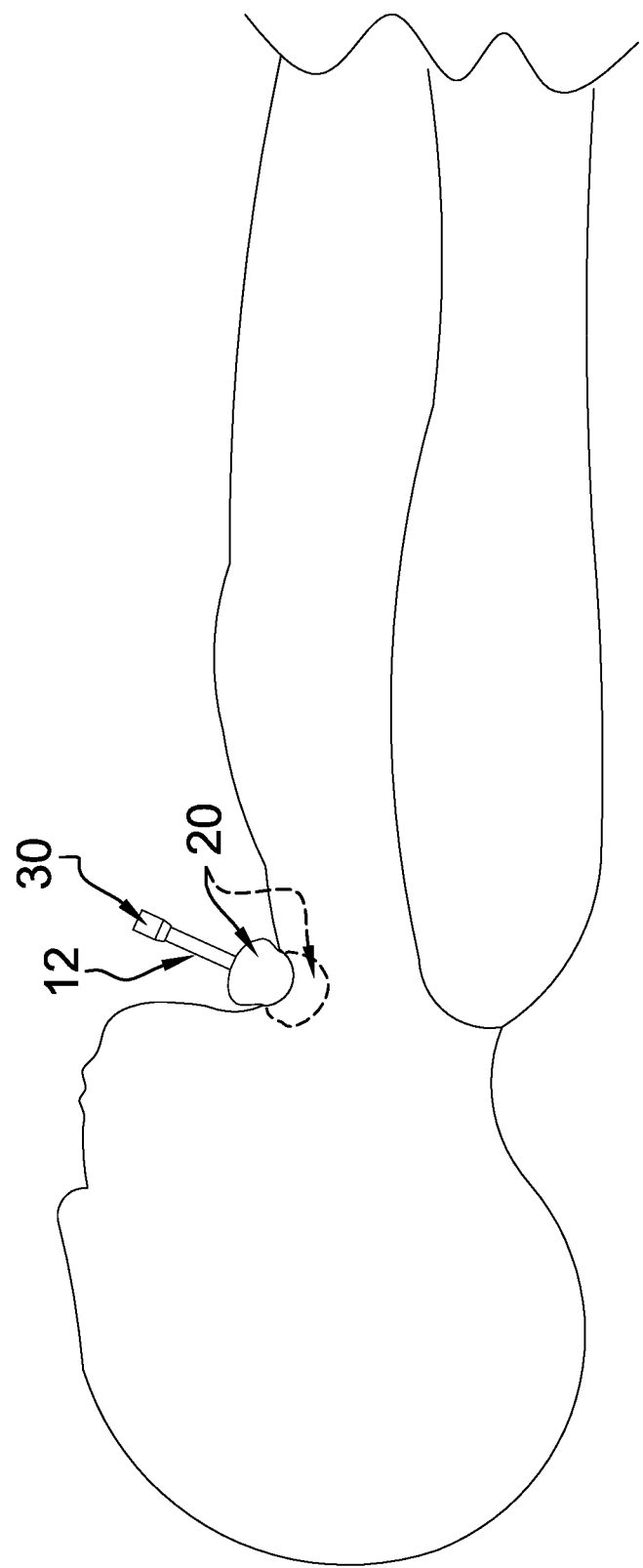
FIG. 6 is an in-use view of an embodiment of the disclosure.

As shown in FIG. 4, the container 18 may comprise a syringe 24, which has a needle 26 engaged thereto. The connector 14 may comprise a disc 28, which is engaged to the tube 12 and which covers the first end 16 of the tube 12. The disc 28 is resiliently stretchable so that the disc 28 is configured for insertion of the needle 26 and to sealably engage the needle 26. The present invention also anticipates the connector 14 comprising other connecting means, such as, but not limited to, a quick connect for coupling to a conduit extending from a pump, a Luer connector for coupling directly to a syringe 24, and the like.

The disc 28 may be integral to a cap 30, which is engaged to the tube 12. The cap 30 is positioned on the tube 12 so that the disc 28 covers the first end 16 of the tube 12. A body 32 of the cap 30 extends radially and outwardly from the tube 12 so that the cap 30 can be used to at least partially close an entrance to the penetrating wound. The body 32 of the cap 30 may be tapered distal from the disc 28 so that the cap 30 is complementary to entrances of penetrating wounds having a variety of circumferences. The cap 30 comprises at least one of elastomer, rubber, and silicone.

In use, the tube 12 is grasped proximate to the first end 16 and used to at least partially insert the shell 20 into the penetrating would. The needle 26 is inserted through the disc 28 and a plunger 34 of the syringe 24 is depressed to force air from the syringe 24 through the needle 26 and the tube 12 into the shell 20. The shell 20 expands to contact and apply pressure to the surface of the penetrating wound to limit hemorrhaging. The needle 26 can be extracted from the disc 28 without loss of pressure, thereby facilitating mobilization of the mammal.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A hemorrhage control device comprising:
a tube;
a connector engaged to a first end of the tube and being configured for selectively engaging a container, such that the container is in fluidic communication with the tube, the container being configured for selectively pressuring a fluid positioned therein, such that the fluid is selectively dispensable from the container through the tube;
a shell engaged to a second end of the tube such that the shell is in fluidic communication with the tube, the shell being selectively expandable from a compacted configuration, wherein the shell is substantially circumferentially equivalent to the tube, wherein the shell is configured for at least partial insertion into a penetrating wound in a mammal, for selectively expanding as the fluid is dispensed from the container through the tube, and for contacting a surface of the penetrating wound for controlling hemorrhaging;
the container comprises a syringe having a needle engaged thereto; and
the connector comprises a disc engaged to the tube and covering the first end of the tube, the disc being resiliently stretchable, wherein the disc is configured for insertion of the needle and for sealably engaging the needle.

2. The hemorrhage control device of claim 1, wherein the tube is semirigid such that the tube is resiliently bendable.

3. The hemorrhage control device of claim 2, wherein the tube comprises plastic.

4. The hemorrhage control device of claim 1, wherein the shell comprises at least one of polyester, nylon, polyether block amide, polyurethane, and silicone.

5. The hemorrhage control device of claim 1, wherein the shell substantially spherically shaped when filled with the fluid.

6. The hemorrhage control device of claim 1, wherein the shell is radiopaque.

7. The hemorrhage control device of claim 1, wherein the disc is integral to a cap engaged to the tube, the cap being positioned on the tube such that the disc covers the first end of the tube, and such that a body of the cap extends radially and outwardly from the tube.

8. The hemorrhage control device of claim 7, wherein the cap comprises at least one of elastomer, rubber, and silicone.

9. The hemorrhage control device of claim 1, wherein the body of the cap is tapered distal from the disc.

10. The hemorrhage control device of claim 1, wherein the fluid comprises air.

11. A hemorrhage control device comprising:
a tube, the tube being semirigid such that the tube is resiliently bendable, the tube comprising plastic;
a connector engaged to a first end of the tube and being configured for selectively engaging a container, such that the container is in fluidic communication with the tube, the container being configured for selectively pressuring a fluid positioned therein, such that the fluid is selectively dispensable from the container through the tube;
a shell engaged to a second end of the tube such that the shell is in fluidic communication with the tube, the shell being selectively expandable from a compacted configuration, wherein the shell is substantially circumferentially equivalent to the tube, wherein the shell is configured for at least partial insertion into a penetrating wound in a mammal, for selectively expanding as the fluid is dispensed from the container through the tube, and for contacting a surface of the penetrating wound for controlling hemorrhaging, the shell comprising at least one of polyester, nylon, polyether block amide, polyurethane, and silicone, the shell being substantially spherically shaped when filled with the fluid, the shell being radiopaque;

the container comprising a syringe having a needle engaged thereto; and the connector comprising a disc engaged to the tube and covering the first end of the tube, the disc being resiliently stretchable, wherein the disc is configured for insertion of the needle and for sealably engaging the needle, the disc being integral to a cap engaged to the tube, the cap being positioned on the tube such that the disc covers the first end of the tube and such that a body of the cap extends radially and outwardly from the tube, the cap comprising at least one of elastomer, rubber, and silicone, the body of the cap being tapered distal from the disc, the fluid comprising air.

* * * * *